United States Patent
Michalski (10) Patent No.: US 9,891,238 B2
(45) Date of Patent: Feb. 13, 2018

(54) DETERMINATION OF THE THROMBOGENIC POWER OF HUMAN IMMUNOGLOBULINS

(75) Inventor: Catherine Michalski, Les Ulis (FR)

(73) Assignee: LABORATOIRE FRANCAIS DU FRACTIONNEMENT ET DES BIOTECHNOLOGIES, Les Ulis (FR)

( * ) Notice: Subject to any disclaimer, the term of this patent is extended or adjusted under 35 U.S.C. 154(b) by 1007 days.

(21) Appl. No.: 14/343,642

(22) PCT Filed: Nov. 18, 2011

(86) PCT No.: PCT/FR2011/052703
§ 371 (c)(1),
(2), (4) Date: Jun. 23, 2014

(87) PCT Pub. No.: WO2012/066260
PCT Pub. Date: May 24, 2012

(65) Prior Publication Data
US 2014/0295471 A1    Oct. 2, 2014

(30) Foreign Application Priority Data
Nov. 18, 2010  (FR) ..................... 10 59493

(51) Int. Cl.
*C12Q 1/56* (2006.01)
*G01N 33/86* (2006.01)
*G01N 33/68* (2006.01)

(52) U.S. Cl.
CPC ......... *G01N 33/86* (2013.01); *G01N 33/6854* (2013.01); *G01N 2333/96463* (2013.01)

(58) Field of Classification Search
CPC ......... G01N 33/86; G01N 2333/96463; G01N 33/6854
See application file for complete search history.

(56) References Cited

U.S. PATENT DOCUMENTS 5,922,587 A * 7/1999 Triplett ............... C07K 14/46
                                                       435/212
2010/0009396 A1   1/2010 Hilbert et al.

FOREIGN PATENT DOCUMENTS

| EP | 1536236 A1 | 6/2005 |
|---|---|---|
| FR | 2910969 A1 | 7/2008 |
| WO | 9638585 A1 | 12/1996 |
| WO | 9719357 A1 | 5/1997 |
| WO | 2009045406 A1 | 4/2009 |
| WO | 2010020423 A2 | 2/2010 |

OTHER PUBLICATIONS

Haematologic Technologies Inc. a brochure on—Immunodepleted factor deficient plasma, 2009, pp. 1-2 ( published on the web on Apr. 4, 2005, at at http://www.haemtech.com/plasma.htm).*
Hemker H.C. et al., "Thrombin generation, a function test of the haemostatic-thrombotic system", Thromb. Haemost., 2006, vol. 96, pp. 553-561.*
Luddington R. et al., "Clinical measurement of thrombin generation by calibrated automated thrombography requires contact factor inhibition", Journal of Thrombosis and Haemostasis, 2004, vol. 2, pp. 1954-1959.*
French Search Report, dated Jul. 5, 2011, from corresponding FR application.
Written Opinion, dated Feb. 9, 2012, from corresponding PCT application.
International Search Report, dated Feb. 9, 2012, from corresponding PCT application.
Galli et al., "Anti-prothrombin IgG from patients with anti-phospholipid antibodies inhibits the inactivation of factor Va by activated protein C", British Journal of Haematology, 2005, vol. 129, pp. 240-247.
Hemker et al., "The technique of measuring thrombin generation with fluorescent substrates: 4. The H-transform, a mathematical procedure to obtain thrombin concentrations without external calibration", New Technologies, Diagnostic Tools and Drugs, Thromb Haemost, 2009, vol. 101, pp. 1-7.
Tardy-Poncet et al., "Thrombin generation and heparin-induced thrombocytopenia", Journal of Thrombosis and Haemostasis, vol. 7, pp. 1474-1481.

* cited by examiner

*Primary Examiner* — Satyendra K Singh
(74) *Attorney, Agent, or Firm* — Young & Thompson (57) ABSTRACT

A kit for the determination of the thrombogenic power of human immunoglobulins contained in a biologically acceptable product. Also a process making it possible to determine the thrombogenic power linked to the presence of activated Factor XI and/or activated Factor IX and/or activated Factor XII, and/or activated Factor VII and/or activated Factor X in a sample capable of being administered to humans.

21 Claims, 11 Drawing Sheets

DETERMINATION OF THE THROMBOGENIC POWER OF HUMAN IMMUNOGLOBULINS

FIELD OF THE INVENTION

The present invention relates to the determination of the thrombogenic power of human immunoglobulins contained in a sample to be tested.

BACKGROUND OF THE INVENTION

Human immunoglobulins, essentially containing IgGs, are commonly used in the treatment of pathologies such as immunodeficiency or auto-immune diseases and particularly by intravenous route (IvIG).

Nevertheless, according to clinical observation, the use of IvIGs in patients sometimes results in serious side effects, such as for example thromboembolic events.

An embolic thrombosis consists of the formation of a thrombus obstructing a blood vessel. The thrombus can develop in the venous circulation and give rise to a venous thrombosis, or in the arterial circulation and result in an arterial occlusion with ischaemia or even infarction. A thrombus results from blood coagulation, due to platelet aggregation and the activation of the coagulation system, this being a chain reaction which involves the platelets and the coagulation factors. A thrombus essentially contains fibrin, an insoluble protein formed from fibrinogen.

Factors XI and IX are among the factors involved in intrinsic pathway blood coagulation. Factor IX is activated by activated Factor XI, the latter itself being activated by activated Factor XII. This activation cascade finally results in the formation of fibrinogen. (FI).

The Applicant's studies presented in the present application have made it possible to show that the presence of coagulation factors such as Factor VII, Factor IX, Factor XI, Factor XII or Factor X and/or their activated forms in a human immunoglobulin product such as IvIGs, could be the cause of thromboembolic events after the injection of IvIGs in patients.

As a result, there is a great need to make available a reliable and sensitive process making it possible to determine the presence of activated factor VII, activated Factor XI, activated factor IX, activated Factor XII and/or activated Factor X in a biologically acceptable product containing immunoglobulins.

The thrombin generation test (TGT) is known to a person skilled in the art. The principle of this test relates to analysis of the kinetics of the formation of thrombin that a given plasma produces in response to a standardized stimulation.

Among the TGTs developed to date, thromboelastography consists of measuring the physical properties of whole blood by mechanically analyzing clot formation as a function of time. According to the parameters extracted from a graph (called a thromboelastogram) produced by a thromboelastographer, it is possible to assess a patient's coagulation ability.

Moreover, in 2002, Hemker et al. proposed the concept of thrombinography making it possible to measure the generation of thrombin by fluorometry (*Pathophysiol Haemost thromb* 2002; 32: 249-53). Thrombinography consists of using a thrombin calibrator and a specific fluorescent substrate in platelet-ploor plasma or in platelet-rich plasma, in order to establish a thrombinogram. A signal induced by the thrombin generated by the tissue factor is confronted with the signal generated by a standardized quantity of exogenous thrombin in this same plasma.

The Applicant of the present application has surprisingly found that a thrombin generation test also makes it possible to determine the presence of FVII, FXI, FIX, FXII, FX and/or of their activated forms in a sample.

SUMMARY OF THE INVENTION

An objective of the present invention is to provide a kit for the determination of the thrombogenic power of human immunoglobulins contained in a biologically acceptable product.

An objective of the present invention is also to provide a process making it possible to determine the thrombogenic power linked to the presence of activated Factor VII, activated Factor XI, activated Factor IX, activated Factor XII and/or activated Factor X in a sample capable of being administered to humans.

The first aspect of the invention relates to the use of a kit comprising the following components:
 a platelet-poor human blood plasma,
 phospholipids,
 $CaCl_2$, and optionally
 human tissue factor,
in order to determine the thrombogenic power of human immunoglobulins contained in a sample to be tested, in particular biologically acceptable, said components of the kit and the sample to be tested forming a reaction medium when they are mixed.

The second aspect of the invention relates to the use of a kit comprising the following components:
 a human blood plasma deficient in Factor XI,
 phospholipids,
 $CaCl_2$, and optionally
 human tissue factor,
in order to determine the thrombogenic power of human immunoglobulins contained in a sample to be tested, in particular biologically acceptable, said components of the kit and the sample to be tested forming a reaction medium when they are mixed.

DETAILED DESCRIPTION OF THE INVENTION

By "human blood plasma deficient in Factor XI", is meant a human blood plasma containing less than 1% (functional and antigenic tests) of the normal quantity of Factor XI and activated Factor XI.

A blood plasma deficient in Factor XI is prepared by immunoadsorption, such as the plasma deficient in Factor XI marketed by Cryopep.

By "human immunoglobulins" or "human IgGs" is meant within the context of the invention, polyvalent immunoglobulins which are essentially IgGs, optionally including IgMs. These can be whole immunoglobulins, or fragments such as F(ab')2 or F(ab) and any intermediate fraction obtained during the polyvalent immunoglobulin manufacturing process.

Within the context of the invention, by "thrombogenic power" is meant the ability of human immunoglobulins to trigger coagulation and form a thrombus in patients. As a result, a "preparation of thrombogenic immunoglobulins" is a preparation of immunoglobulins having the ability to induce coagulation and form a thrombus in patients.

Given that coagulation factors are naturally present in human plasmas, the thrombogenic power of immunoglobulins is a relative index with respect to the blood coagulation that can be triggered naturally in patients.

By a "biologically acceptable" sample, is meant a sample capable of being administered to humans by intravenous, parenteral, or intramuscular route. It may in particular be human immunoglobulin preparations for therapeutic use.

By "preparations of human immunoglobulins for therapeutic use" is meant any medicament comprising human immunoglobulins in a pharmaceutically acceptable form. It can in particular be IvIG.

The use of the kit according to the present invention makes it possible to establish a thrombinogram for the sample to be tested. A thrombinogram is represented by a thrombin generation curve characterized by several parameters:

The latency or lag time (in minutes) which is correlated to the coagulation time The area under the peak or ETP (Endogenous Thrombin Potential, in nM×min), directly correlated to the total quantity of thrombin generated The peak height (in nM), representing the maximum quantity of thrombin present in the sample during reading The time to peak: ttPeak (in minutes), which is the time making it possible to reach the top of the peak The velocity: Peak/(ttPeak-lag time) (in nM/min), representative of the rate of formation of the thrombin.

Advantageously, the invention relates to the use of a kit comprising the following components:

a platelet-poor human blood plasma deficient in Factor XI,
phospholipids,
$CaCl_2$, and optionally
human tissue factor, in order to determine the thrombogenic power, linked to the presence in particular of Factor VII, Factor XI, Factor IX, Factor X and/or their activated forms, human immunoglobulins contained in a sample to be tested, in particular biologically acceptable, said components of the kit and the sample to be tested forming a reaction medium.

Even more advantageously, the invention relates to the use of a kit comprising the following components:

a platelet-poor human blood plasma,
phospholipids,
CaCl2, and optionally
human tissue factor, in order to determine the thrombogenic power, linked to the presence in particular of Factor XII and/or its activated form, human immunoglobulins contained in a sample to be tested, in particular biologically acceptable, said components of the kit and the sample to be tested forming a reaction medium.

By "platelet-poor human blood plasma deficient in Factor XI", is meant a human blood plasma containing less than 1% (functional and antigenic tests) of the normal quantity of Factor XI and less than $10 \times 10^9$ platelets/L of plasma.

A platelet-poor blood plasma is prepared according to a method known to a person skilled in the art, such as centrifugation.

By "activated Factor VII" or "aFVII", is meant an FVII protein capable of activating Factor IX or Factor X.

By "activated Factor XII" or "aFXII", is meant an FXII protein capable of activating Factor XI.

By "activated Factor XI" or "aFXI", is meant a protein constituted by two 80 kDa sub-units, linked to each other by a disulphide bridge at the position Cys-321 and capable of recognizing its natural substrate: FIX.

By "activated factor IX" or "aFIX", is meant an FIX protein capable of recognizing its natural substrate: FX.

By "activated Factor X" or "aFX", is meant an FX protein capable of recognizing its natural substrate, prothrombin.

In a particular embodiment, the present invention relates to the use of a kit according to the invention also comprising a dilution buffer such as a Tris NaCl physiological buffer or a buffer identical to that of the sample to be tested. It is then a buffer with a formulation that is acceptable for a preparation of immunoglobulins for therapeutic use.

The sample of human blood plasma contained in the kit and the dilution buffer form a negative control.

In a particular embodiment, the kit according to the invention also comprises a fluorogenic or fluorescent substrate.

The human blood plasma is taken from healthy volunteer donors having no serious diseases, and contains all the coagulation factors, at normal levels, involved in intrinsic pathway blood coagulation.

In an advantageous embodiment, the human blood plasma is a pool of fresh or frozen human blood plasmas or a calibrated commercial blood plasma.

The blood plasma used in the invention can contain or be devoid of tissue factor.

In an advantageous embodiment, the human blood plasma is devoid of tissue factor.

In an advantageous embodiment, the human tissue factor in the kit is of plasma origin, of recombinant origin, or of transgenic origin.

In a particularly advantageous embodiment, the invention relates to the use of a kit comprising:

a platelet-poor human blood plasma deficient in FXI, the volume of which represents from 80% to 40%, in particular from 75% to 50%, particularly 53% of the volume of the reaction medium.

human phospholipids, the final concentration of which in the reaction medium is from 1 µM to 10 µM, particularly 4 µM, human tissue factor, the final concentration of which in the reaction medium is from 0.05 pM to 10 pM, particularly 0.3 pM, $CaCl_2$.

Said kit can also comprise a dilution buffer, in particular Tris NaCl buffer.

In an advantageous embodiment, the ratio between the volume of the blood plasma and that of the sample to be tested is from 8:1 to 2:1, particularly 4:1.

The ratio of 8:1 to 2:1 corresponds to the conditions of injection of the immunoglobulin into the patient. The ratio of 4:1 is physiologically significant for an Ig concentration of 5%.

Another aspect of the invention relates to a process for measuring the thrombogenic power of human immunoglobulins contained in a sample to be tested, in particular biologically acceptable.

Said process comprises the following stages:

a) mixing the dilution buffer, in particular Tris NaCl buffer, with a platelet-poor human blood plasma in order to form an intermediate negative control;

b) mixing a sample to be tested with the platelet-poor human blood plasma in order to form an intermediate reaction medium;

c) addition to the intermediate reaction medium obtained in the previous stage and to the intermediate negative control obtained in stage a) of a mixture comprising phospholipids, $CaCl_2$, and optionally human tissue factor, in order to form a reaction medium and a negative control;

d) obtaining a first thrombinogram by carrying out a thrombin generation test on the reaction medium obtained in stage c) and a second thrombinogram by carrying out a thrombin generation test on the negative control obtained in stage c);

e) comparison of at least one of the parameters of each of the thrombinograms obtained in stage d) with an homologous parameter obtained from standard thrombinograms established on the basis of a series of calibrators the thrombogenic power of which, linked to the presence of activated Factor VII and/or activated Factor XI and/or activated Factor IX and/or activated Factor XII and/or activated Factor X, is known and varies between each calibrator;

f) deduction from stage e) of the thrombogenic power of human immunoglobulins contained in the sample to be tested.

In a particular embodiment, the platelet-poor human blood plasma is deficient in Factor XI.

In a particular embodiment, the standard thrombinogram is obtained by carrying out a thrombin generation test on a reaction medium comprising i) a calibrator the thrombogenic power of which linked to the presence of activated Factor VII and/or activated Factor XI and/or activated Factor IX and/or activated Factor XII and/or activated Factor X is known, ii) a platelet-poor human blood plasma optionally deficient in Factor XI, iii) a reaction mixture comprising phopholipids, $CaCl_2$ and optionally human tissue factor. The calibrator is used by the software in order to make corrections to the raw signals and makes it possible to remedy certain drawbacks of the fluorescence and to convert the signal initially in fluorescence units per minute directly to nanomolars of thrombin.

In another particular embodiment, the final concentration of human tissue factor in the reaction medium is from 0.05 pM to 10 pM, particularly 0.3 pM. The tissue factor and the aFVII form a complex in order to activate Factors IX and X at the level of the exogenous coagulation pathway.

In another particular embodiment, the final concentration of the human phospholipids in the reaction medium is from 1 µM to 10 µM, particularly 4 µM.

In another particular embodiment, the volume of the blood plasma represents from 80% to 40%, in particular from 75% to 50%, particularly 53% of the volume of the reaction medium.

In another particular embodiment, the ratio between the volume of the blood plasma and that of the sample is from 8:1 to 2:1, particularly 4:1.

In another particular embodiment, the thrombinogram is obtained by the thromboelastography method or the thrombinography method.

The thromboelastography can be implemented according to the method known to a person skilled in the art, as described by Savry et al. (*Ann Fr Anesth Reanim* 2005; 24:607-16).

The thrombinography can be implemented according to the method known to a person skilled in the art, as described by Hemker et al. (*Pathophysiol Haemost thromb* 2002; 32: 249-53).

In a particularly advantageous embodiment, the process according to the invention comprises the following stages:

a) mixing the dilution buffer of a sample to be tested with a platelet-poor human blood plasma deficient in Factor XI in order to form an intermediate negative control;

b) mixing a sample with a platelet-poor human blood plasma deficient in Factor XI representing 53% of the volume of the reaction medium, in which the ratio between the volume of the blood plasma and that of the sample is from 8:1 to 2:1, particularly 4:1 in order to form an intermediate reaction medium;

c) addition to the intermediate reaction medium obtained in the previous stage and in the intermediate negative control obtained in stage a) of a mixture comprising 4 µM of phopholipids, and 0.3 pM of human tissue factor and of $CaCl_2$, in order to form a reaction medium and a negative control;

d) obtaining two thrombinograms by the implementation of thrombinography, by carrying out a thrombin generation test on the reaction medium and on the negative control obtained in stage c);

e) comparison of at least one of the parameters of each of the thrombinograms obtained in stage d) to an homologous parameter obtained from standard thrombinograms established on the basis of a series of calibrators the thrombogenic power of which linked to the presence of activated Factor VII and/or activated Factor XI and/or activated Factor IX and/or activated Factor X is known and varies between each calibrator;

f) deduction from stage e) of the thrombogenic power linked to the presence of Factor VII, Factor XI, Factor IX, Factor X and/or of their activated form in the sample.

The present invention is further illustrated by the figures and the examples below. These figures and examples representing the particular embodiments of the invention, are in no way intended to limit the scope of the invention.

EXAMPLES

Example 1: Determination of the Thrombogenic Power of a Sample

Protocol 1 for Determining the Thrombogenic Power of a Sample to be Tested
Equipment: CAT system (Stago) Reagents: Stago
Normal Plasma: pool of frozen plasma (internal)
Preparation of the samples: 1 volume of product for 8 volumes of NP or of NP at ⅕th in dilution buffer (R1).
Experimental conditions:
    80 µL Preparation. +20 µL PPP-reagent High (4 µM phospholipids and 20 pM TF final)

20 µL FluCa-reagent added by the device
Fluorescence: λ excitation=390 nm, λ emission=460 nm Protocol 2 for Determining the Thrombogenic Power of a Sample to be Tested
- Equipment: Fluoroscan/CAT system (Stago) Reagents: Stago
- Normal Plasma (NP): Pool of frozen plasma (internal) or Unicalibrator (Stago)
- Preparation of the samples: 1 vol of product per 4 or 8 vol of NP
- reaction mixture: 500 µL MP-reagent taken up with 0.5 mL of water+300 µL PRP-reagent+200 µL of dilution buffer
- Experimental conditions:
  - 80 µL Preparation
  - 20 µL reaction mixture (4 µM phospholipids and 0.3 pM TF final)
  - 20 µL FluCa-reagent added by the device
  - Fluorescence: λ excitation=390 nm, λ emission=460 nm The reaction conditions according to Protocol 1 or Protocol 2 are summarized in the table below.

| Equipment | Protocol 1 | Protocol 2 | |
|---|---|---|---|
| | Fluoroscan system CAT (Hemker) | | |
| Plasma | Normal pure | Normal 1/5 = R1 | Normal pure or FXI deficient |
| Tissue Factor | Stago PPP-reagent | Stago PPP-reagent | Stago PRP-reagent |
| Phospholipids | High | High | Stago MP-reagent |
| Fluorogenic substrate | FluCa kit Stago CaCl$_2$ | FluCa kit Stago CaCl$_2$ | FluCa kit Stago CaCl$_2$ |
| TF final | 20 pM | 20 pM | 0.3 pM |
| PL final | 4 µM | 4 µM | 4 µM |
| Plasma final | 59% | 12% | 53% |
| Plasma/Sample | 8:1 | 8:5 | 4:1 |

Example 2: Final Concentration of Tissue Factor

The thrombogenic power of aFXI in a pool of normal plasma or in a pool of diluted plasma is determined according to Protocol 1 (FIG. 1) or Protocol 2 (FIG. 2), respectively described above.

Figure 1:
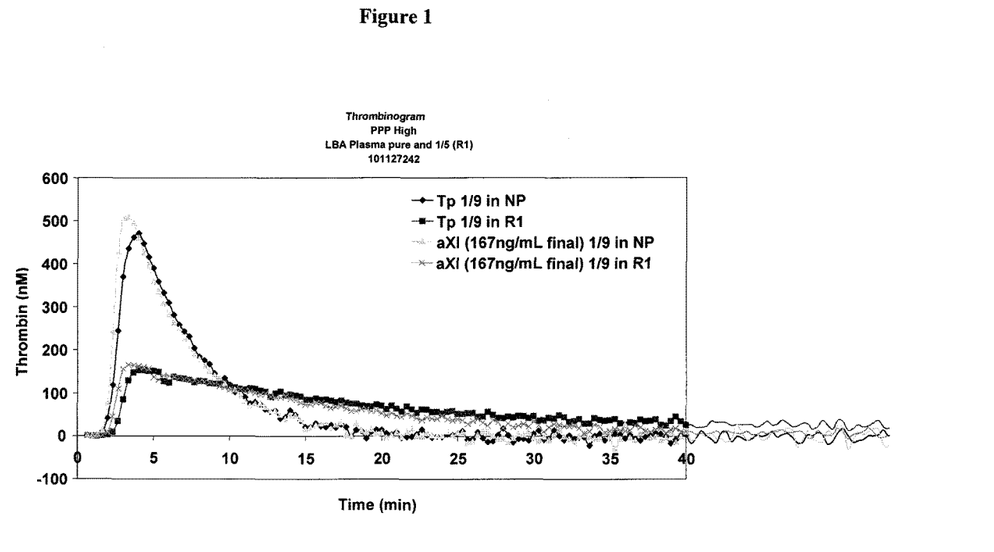
FIG. 1 represents the respective determination of the thrombogenic power of activated Factor XI in a pool of normal plasma, or a pool of diluted normal plasma (1/9), of the dilution buffer in a pool of normal plasma, or a pool of diluted normal plasma (1/9) respectively, according to the first protocol. The final concentration of the tissue factor in the reaction medium is 20 pM. The other reaction conditions are described in Table 1, in the column headed "Protocol 1".
Figure 2:
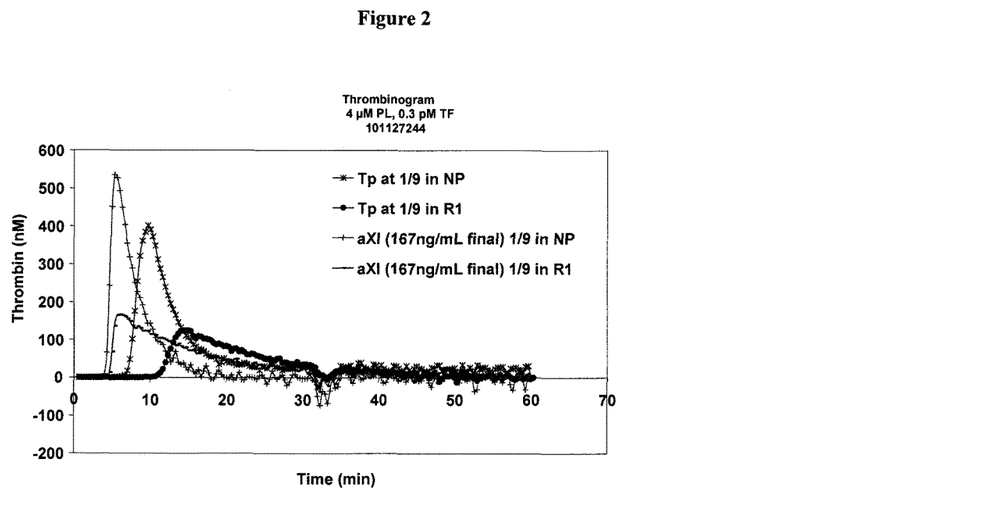
FIG. 2 represents the respective determination of the thrombogenic power of activated Factor XI in a pool of normal plasma, or of aFXI in a pool of diluted normal plasma (1/9), and of the dilution buffer in a pool of normal plasma, or of the dilution buffer in a pool of diluted normal plasma (1/9), according to the second protocol. The final concentration of tissue factor in the reaction medium is 0.3 pM. The other reaction conditions are described in Table 1, in the column headed "Protocol 2".

Protocol 2, carried out at a low final concentration of tissue factor, makes it possible to obtain a result more sensitive than that obtained by Protocol 1, using a high final concentration of tissue factor.

Example 3: Presence of Tissue Factor in the Reaction Medium

Figure 3:
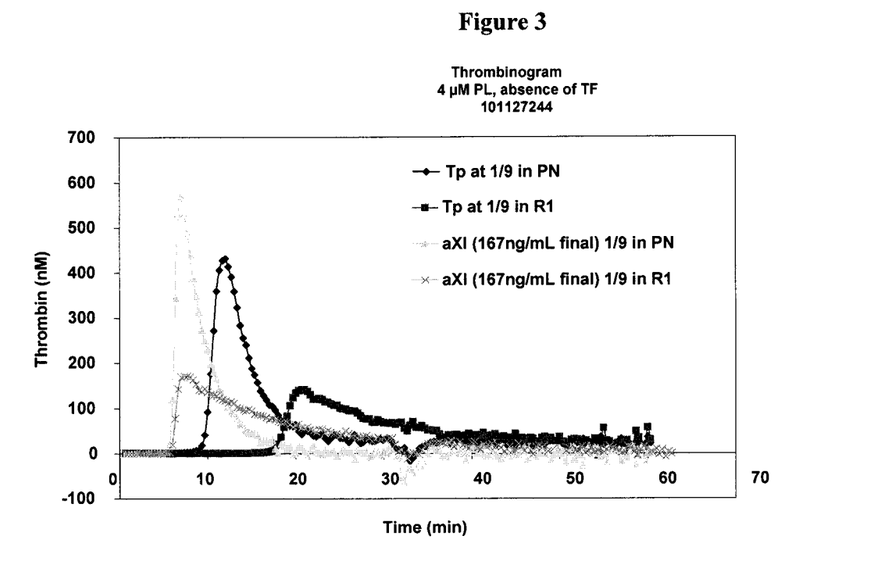
FIG. 3 represents the respective determination of the thrombogenic power of activated Factor XI in a pool of normal plasma, of FXI in a pool of diluted normal plasma (1/9), of dilution buffer in a pool of normal plasma, or of dilution buffer in a pool of diluted normal plasma (1/9), according to the second protocol. The reaction medium contains no tissue factor. The other reaction conditions are described in Table 1, in the column headed "Protocol 2".

The thrombogenic power of aFXI in a pool of normal plasma or in a pool of diluted plasma is determined, according to Protocol 2, in a reaction medium containing 0.3 pM of tissue factor (FIG. 2) or without tissue factor (FIG. 3).

The variability of the responses obtained in the reaction medium without TF is greater than that in the reaction medium with TF. In the absence of TF, the specificity of this response which occurs at later times (>20 min) is not assured.

Example 4: Final Concentration of the Phospholipids

The thrombogenic power of the aFXI in a pool of calibrated commercial plasma (Unicalibrator®, Stago) is determined, according to Protocol 2, in a reaction medium containing 4 µM (FIG. 8) or 8 µM (FIG. 13) of the phospholipids and without TF.

Figure 8:
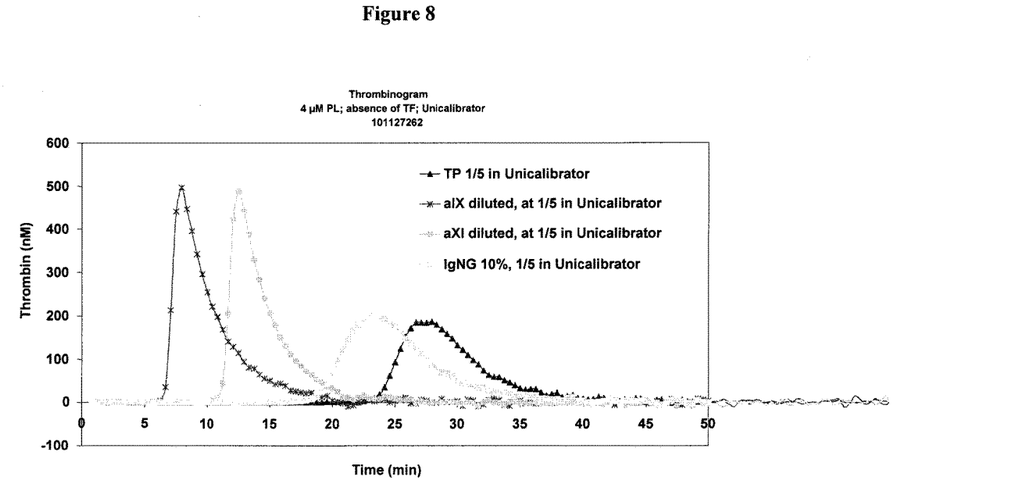
FIG. 8 represents the respective determination of the thrombogenic power of the "Unicalibrator®" plasma containing the dilution buffer, of "Unicalibrator®" plasma containing activated Factor IX, of "Unicalibrator®" plasma containing activated Factor XI, of "Unicalibrator®" plasma containing IgNG-type immunoglobulins. The reaction medium contains no tissue factor. The other reaction conditions are described in Table 1, in the column headed "Protocol 2".
Figure 13:
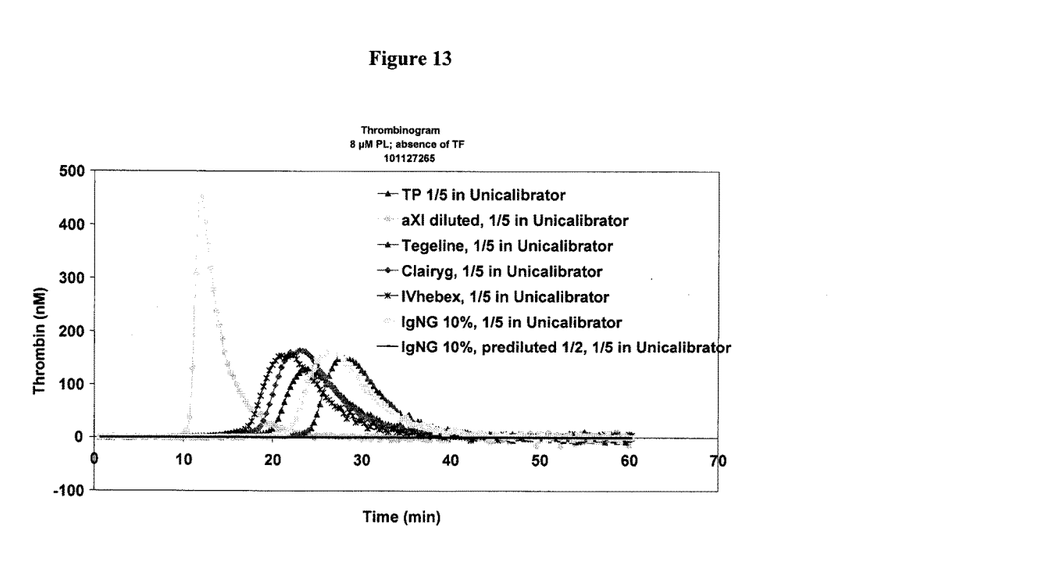
FIG. 13 represents the respective determination of the thrombogenic power of the dilution buffer in the "Unicalibrator®" plasma, of the aFXI in the "Unicalibrator®" plasma, of the Tegeline-type immunoglobulins in the "Unicalibrator®" plasma, of the Clairyg-type immunoglobulins in the "Unicalibrator®" plasma, of the IVhebex-type immunoglobulins in the "Unicalibrator®" plasma, of the IgNG-type 10% immunoglobulins in the "Unicalibrator®" plasma, of the IgNG-type 5% immunoglobulins in the "Unicalibrator®" plasma. The reaction medium contains no tissue factor. The final concentration of the phospholipids in the reaction medium is 8 µM. The other reaction conditions are described in Table 1, in the column headed "Protocol 2".

It appears that the increase in the phospholipids concentration from 4 µM to 8 µM in the absence of tissue factor has not made it possible to stabilize the responses.

Example 5: Determination of the Thrombogenic Power of the IgNG-Type Immunoglobulins Protocol 2 described above is implemented in order to determine the thrombogenic power linked to the presence of aFXI (FIG. 4) or aFIX (FIG. 5) of the IgNG-type immunoglobulins (LFB).

Figure 4:
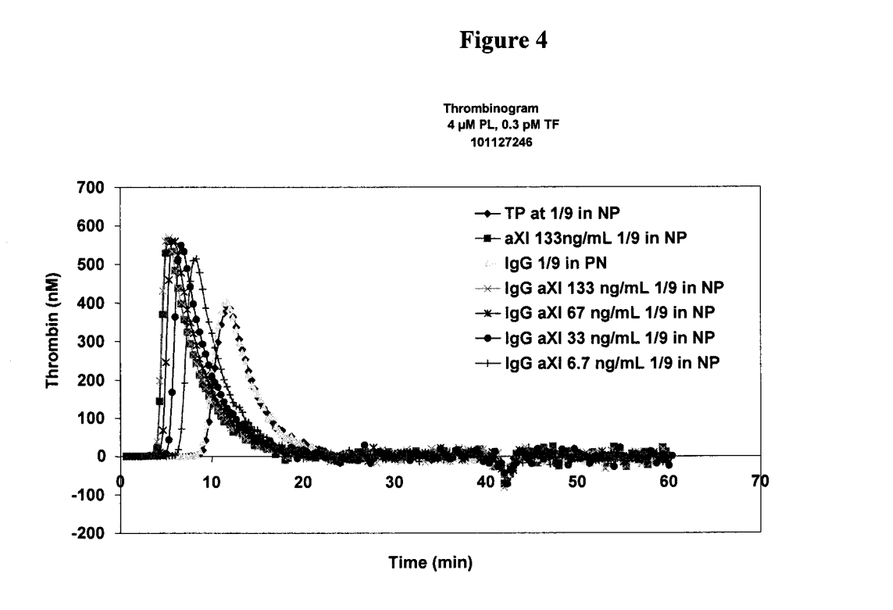
FIG. 4 represents the respective determination of the thrombogenic power of activated Factor XI of different concentrations in a pool of normal plasma containing IgG, of activated aXI in a pool of normal plasma, of a pool of normal plasma containing IgG, and of the dilution buffer in a pool of normal plasma, according to the second protocol. The final concentration of tissue factor in the reaction medium is 0.3 pM. The other reaction conditions are described in Table 1, in the column headed "Protocol 2".
Figure 5:
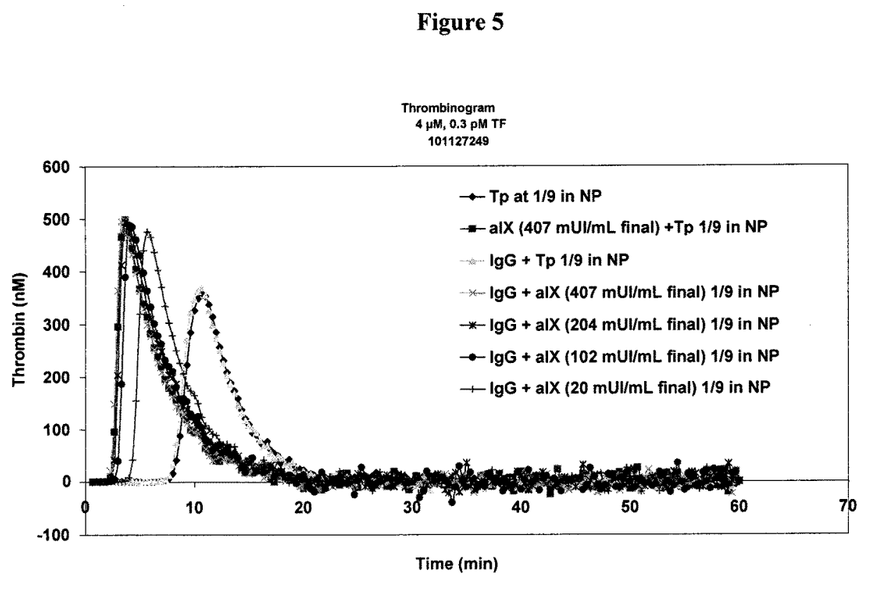
FIG. 5 represents the respective determination of the thrombogenic power of activated Factor IX of different concentrations in a pool of normal plasma containing IgG, of activated aIX in a pool of normal plasma, of a pool of normal plasma containing IgG, and of the dilution buffer in a pool of normal plasma, according to the second protocol. The final concentration of tissue factor in the reaction medium is 0.3 pM. The other reaction conditions are described in Table 1, in the column headed "Protocol 2".

The signal of the appearance of thrombin in the sample containing IgNG-type immunglobulins only, appeared virtually at the same time as that of the appearance of thrombin in the sample containing the dilution buffer. It appears that the IgNG-type immunoglobulins contain virtually no aFXI or aFIX.

Example 6: Origin of the Pool of Blood Plasma

Figure 7:
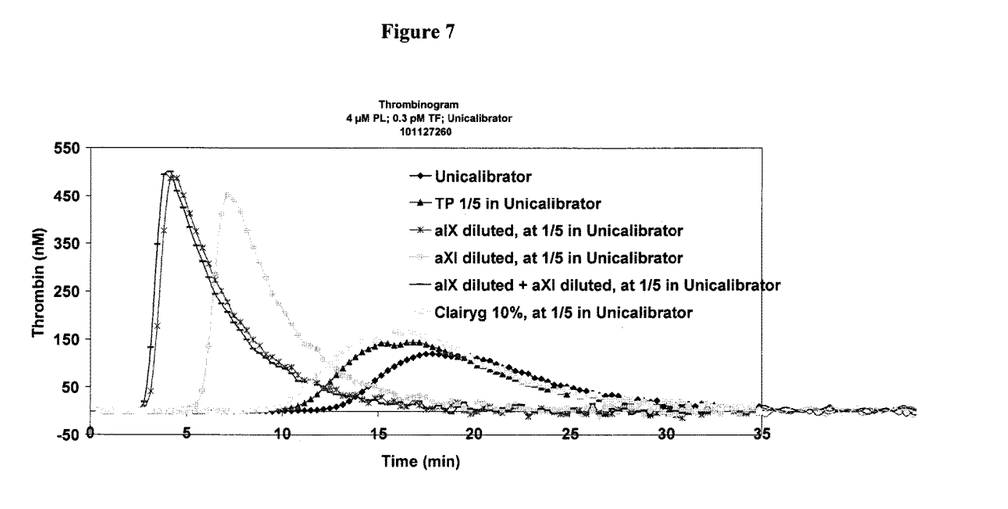
FIG. 7 represents the respective determination of the thrombogenic power of the calibrated plasma marketed by Stago under the name "Unicalibrator®", "Unicalibrator®" plasma containing the dilution buffer, of "Unicalibrator®" plasma containing activated Factor IX, of "Unicalibrator®" plasma containing activated Factor XI, "Unicalibrator®" plasma containing activated Factor IX and activated Factor XI, of "Unicalibrator®" plasma containing Clairyg®-type immunoglobulins. The final concentration of tissue factor in the reaction medium is 0.3 pM. The other reaction conditions are described in Table 1, in the column headed "Protocol 2".
Figure 9:
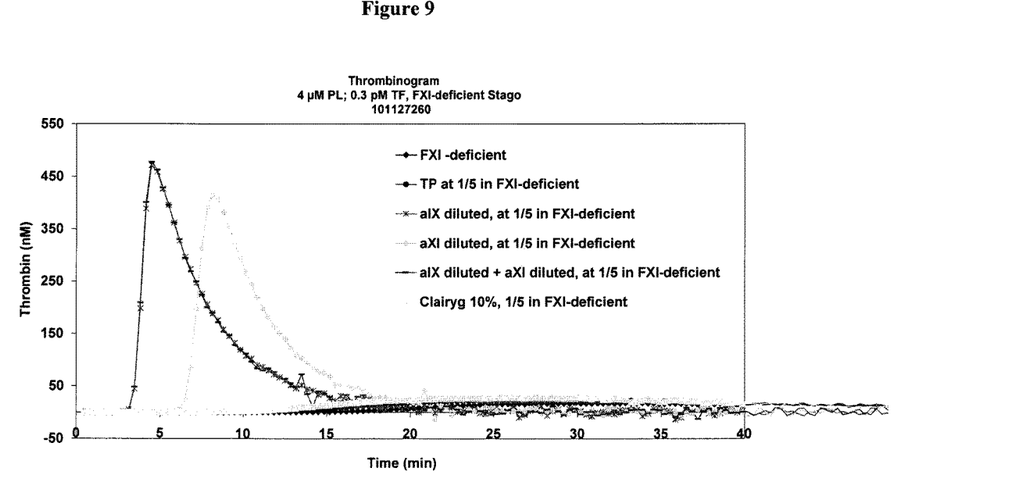
FIG. 9 represents the respective determination of the thrombogenic power of the plasma deficient in FXI, of aFIX in a plasma deficient in FXI, of aFXI in a plasma deficient in FXI, of aFIX and of aFXI in a plasma deficient in FXI, of Clairyg®-type immunoglobulins in a plasma deficient in FXI. The final concentration of tissue factor in the reaction medium is 0.3 pM. The other reaction conditions are described in Table 1, in the column headed "Protocol 2".
Figure 10:
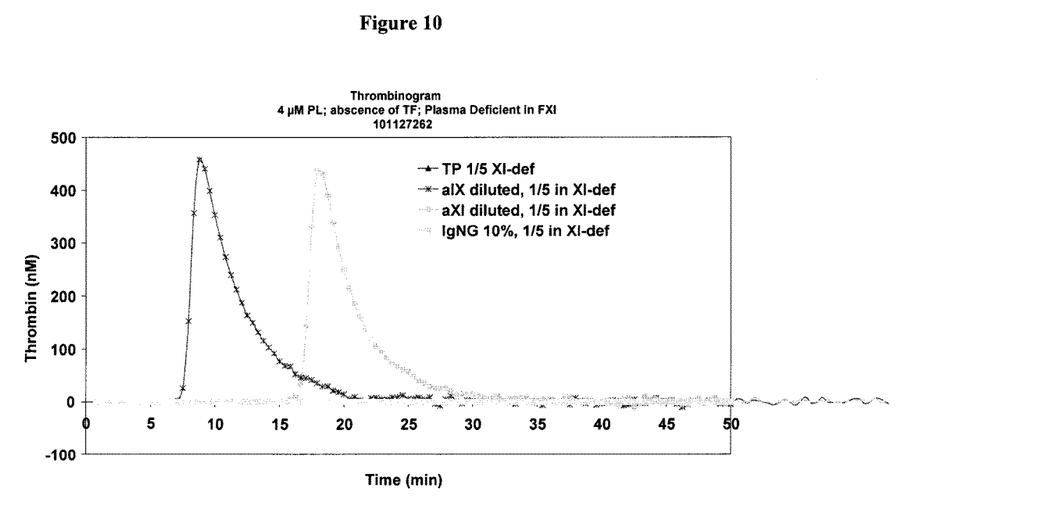
FIG. 10 represents the respective determination of the thrombogenic power of the plasma deficient in FXI, of the aFIX in a plasma deficient in FXI, of the aFXI in a plasma deficient in FXI, of the IgNG-type immunoglobulins in a plasma deficient in FXI. The reaction medium contains no tissue factor. The other reaction conditions are described in Table 1, in the column headed "Protocol 2".
Figure 11:
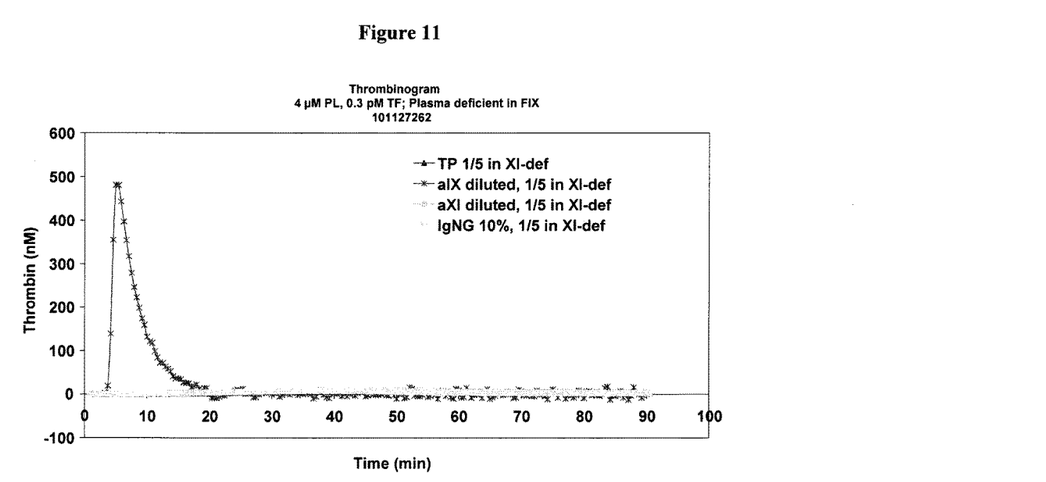
FIG. 11 represents the respective determination of the thrombogenic power of the plasma deficient in FIX, of the aFIX in a plasma deficient in FIX, of the aFIX in a plasma deficient in FIX, of the IgNG-type immunoglobulins in a plasma deficient in FIX. The final concentration of tissue factor in the reaction medium is 0.3 pM. The other reaction conditions are described in Table 1, in the column headed "Protocol 2".
Figure 12:
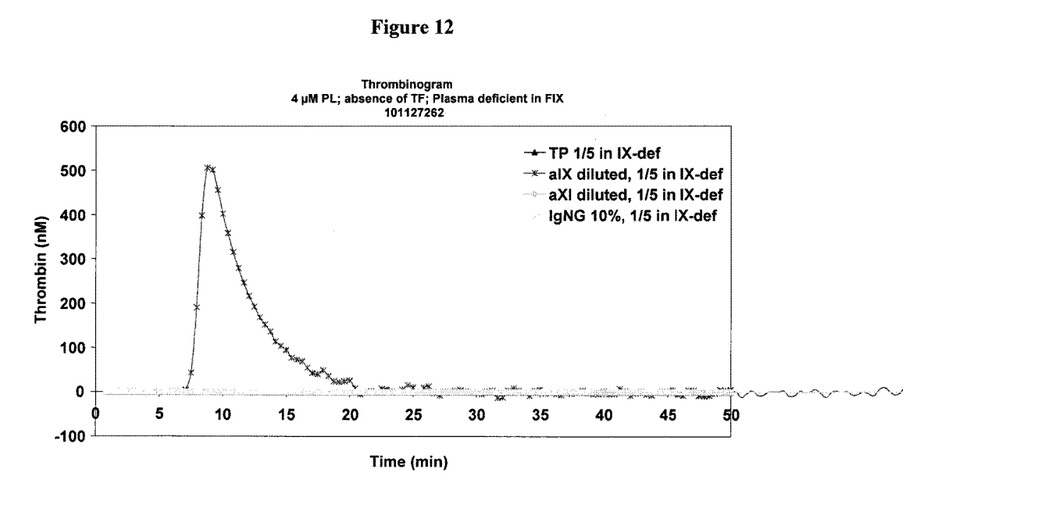
FIG. 12 represents the respective determination of the thrombogenic power of the plasma deficient in FIX, of the aFIX in a plasma deficient in FIX, of the aFIX in a plasma deficient in FIX, of the IgNG-type immunoglobulins in a plasma deficient in FIX. The reaction medium contains no tissue factor. The other reaction conditions are described in Table 1, in the column headed "Protocol 2".

The thrombogenic power of aFXI or aFIX is determined, according to Protocol 2, in a reaction medium containing respectively a pool of calibrated commercial normal plasma (Unicalibrator®) (FIGS. 7 and 8), a pool of plasma deficient in FXI (FIGS. 9 and 10), or a pool of plasma deficient in FIX (FIGS. 11 and 12).

The discriminating ability of the signal vis-à-vis a sample containing aFXI in a reaction medium containing a pool of commercial plasma is not significantly different from that in a pool of plasma deficient in FXI (FIGS. 12, 13, 14 and 15).

It appears that the modifications observed between the results obtained in the reaction media containing different plasma pool origins are very small.

Example 7: Thrombogenic Power of Different Immunoglobulins

The respective thrombogenic power of the Tegeline®-type immunoglobulins (LFB), Clairyg®-type immunoglobulins (LFB), IvHEBEX®-type immunoglobulins (LFB), and IgNG-type immunoglobulins (LFB), linked to the presence of aFXI and/or aFIX, is determined according to Protocol 2.

Figure 6:
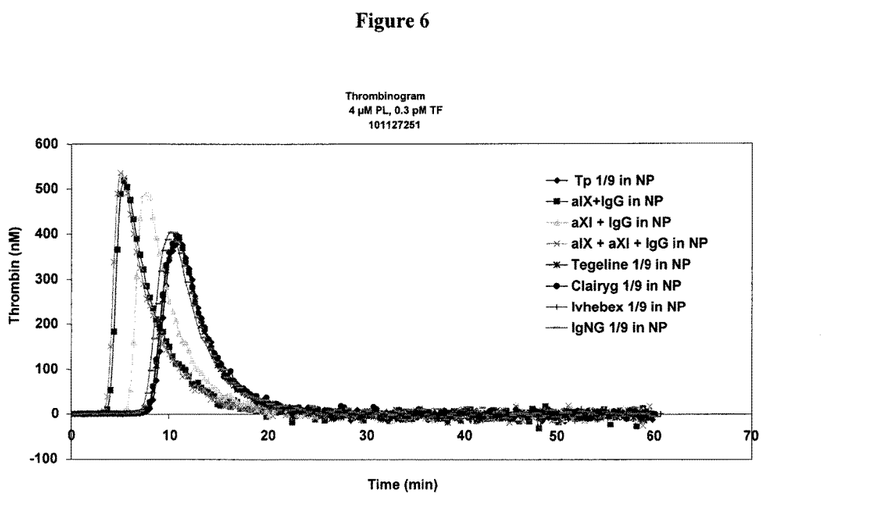
FIG. 6 represents the respective determination of the thrombogenic power of the dilution buffer in a pool of normal plasma, of activated Factor XI in a pool of normal plasma containing IgG, of activated Factor IX in a pool of normal plasma containing IgG, of activated Factor XI and of activated Factor IX in a pool of normal plasma containing IgG, of the Tegeline®-type immunoglobulins (LFB) in a pool of normal plasma containing Clairyg®-type immunoglobulins (LFB) in a pool of normal plasma, of the IgNG-type immunoglobulins (LFB) in a pool of normal plasma, of IVHEBEX®-type immunoglobulins (LFB) in a pool of normal plasma. The final concentration of tissue factor in the reaction medium is 0.3 pM. The other reaction conditions are described in Table 1, in the column headed "Protocol 2".

The results are illustrated by FIG. 6.

Example 8: Inhibition of the aFXI Potential of Thrombogenic Ig Preparation

Figure 14A:
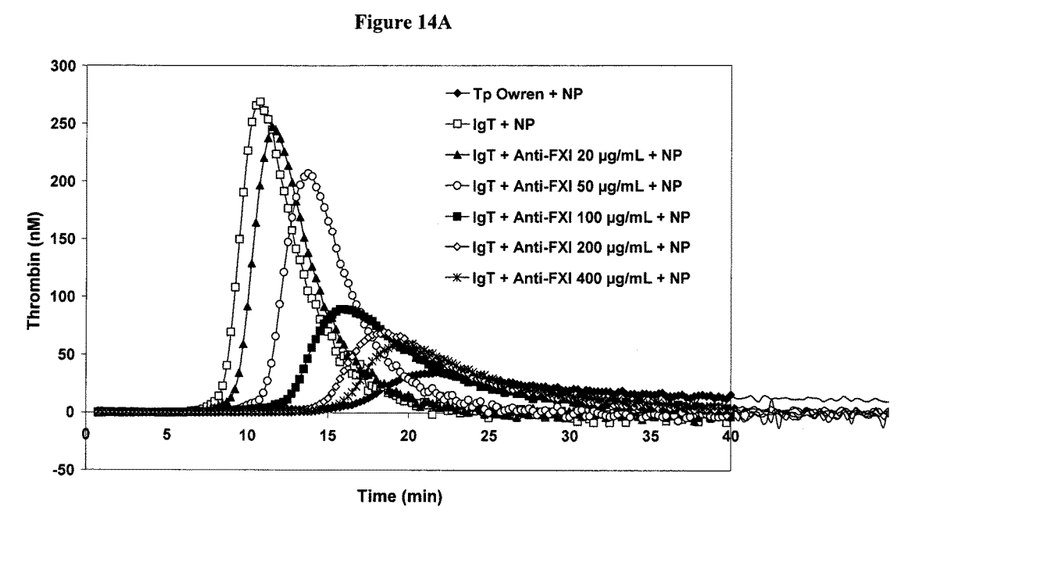
FIG. 14A represents the respective determination of the thrombogenic power of the samples containing 0.3 pM of tissue factor, 4 µM of phospholipids, 10 µL of thrombogenic intravenous immunoglobulin, 80 µL of normal plasma and optionally 10 µL of anti-FXI.
Figure 14B:
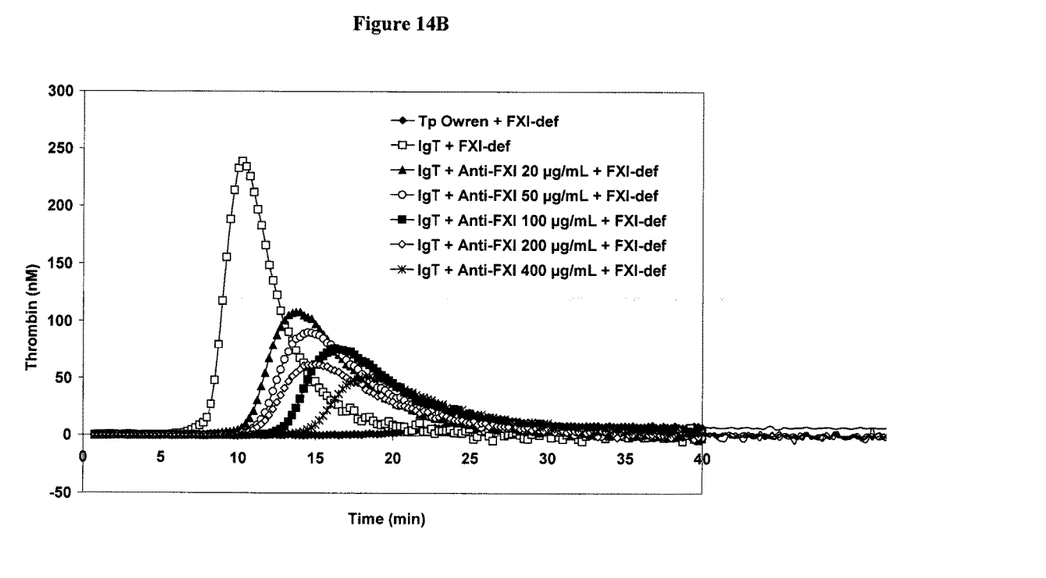
FIG. 14B represents the respective determination of the thrombogenic power of the samples containing 0.3 pM of tissue factor, 4 µM of phospholipids, 10 µL of thrombogenic intravenous immunoglobulin, 80 ∞L of plasma deficient in FXI and optionally 10 µl of anti-FXI.

A range of anti-human aFXI monoclonal bodies, from 20 to 400 µg/ml was produced and tested in the presence of thrombogenic Ig (TIg) preparation, in normal plasma (FIG. 14A) and deficient in FXI (FIG. 14B).

An inhibition of the thrombogenic potential of the pure tested Ig as a function of increasing doses of anti-FXI antibody was observed. The inhibition is not total at the highest concentration of anti aFXI of 400 µg/ml.

In order to limit the consumption of the antibody, the same test was repeated on the same batch of immunoglobulin diluted at 1/10 and 1/30. The same doses of antibody were tested from 20 to 400 µg/ml.

Under these conditions, a total inhibition of exogenous aFXI (immunoglobulin) and of aFXI originating from the zymogenous FXI is observed in the case of the normal plasma: a plateau phenomenon is observed.

Figure 15:
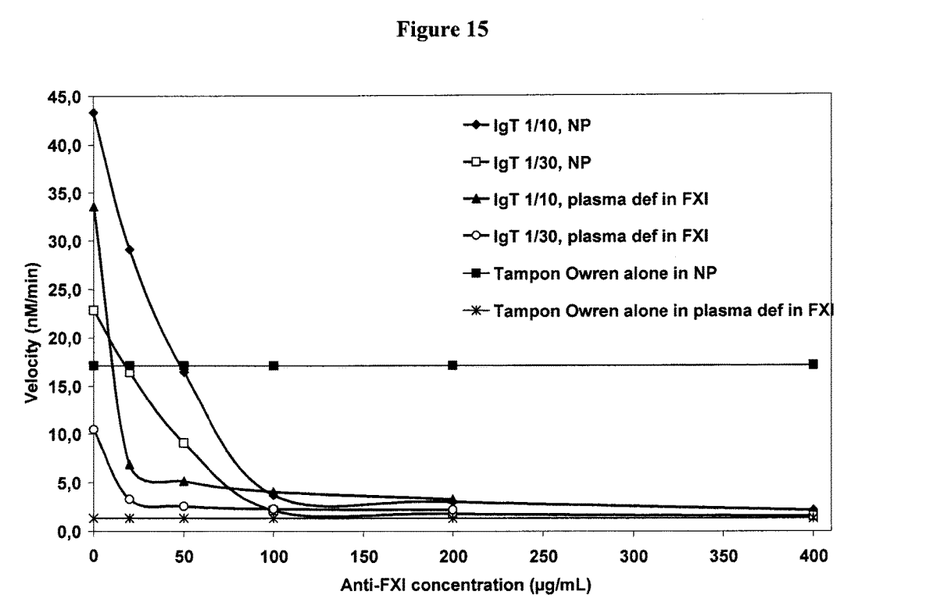
FIG. 15 represents the study of the velocity as a function of the concentration of FXI inhibitor.

FIG. 15 shows the velocity parameter as a function of the doses of anti-aFXI antibody, in normal plasma and in plasma deficient in aFXI.

In normal plasma, the inhibition is at a maximum in the case of the dose of 100 µg/ml of antibody at the 2 dilutions of Ig tested. In this case, the thrombinogram obtained shows a velocity below that of the dilution buffer tested alone in normal plasma, the activated FXI originating from the plasma also being inhibited.

In plasma deficient in FXI and aFXI, the inhibition is complete in the case of a lower dose of 50 µg/ml of antibody. In this case, a velocity comparable to that of the dilution buffer alone in plasma deficient in FXI and aFXI is again found. This result shows that, for this batch, the exogenous aFXI alone is responsible for the increase in thrombic potential.

These results demonstrate that:
The thrombin generation peak observed for the preparation of thrombogenic Ig tested is indeed linked to the presence of aFXI.
The use of a test sensitive to aFXI for the study of the thrombic potential of batches of immunoglobulins is relevant.

Example 9: Research into a Possible Inhibitory Effect on the Generation of Thrombin: Protein Environment As the batches of immunoglobulins were highly concentrated (50 g/l), it was verified that this environment had no impact (inhibitory effect) on the generation of thrombin. Such a phenomenon would in fact lead to the conclusion of a falsely negative result.

A range of aFXI from 1 to 15 ng/ml was produced (FIG. 16); the dilutions were made in parallel in a batch of 5% IgNG (aFXI+IgNG curves) and in the buffer with the 5% IgNG formulation (aFXI+Tp curves).

Figure 16:
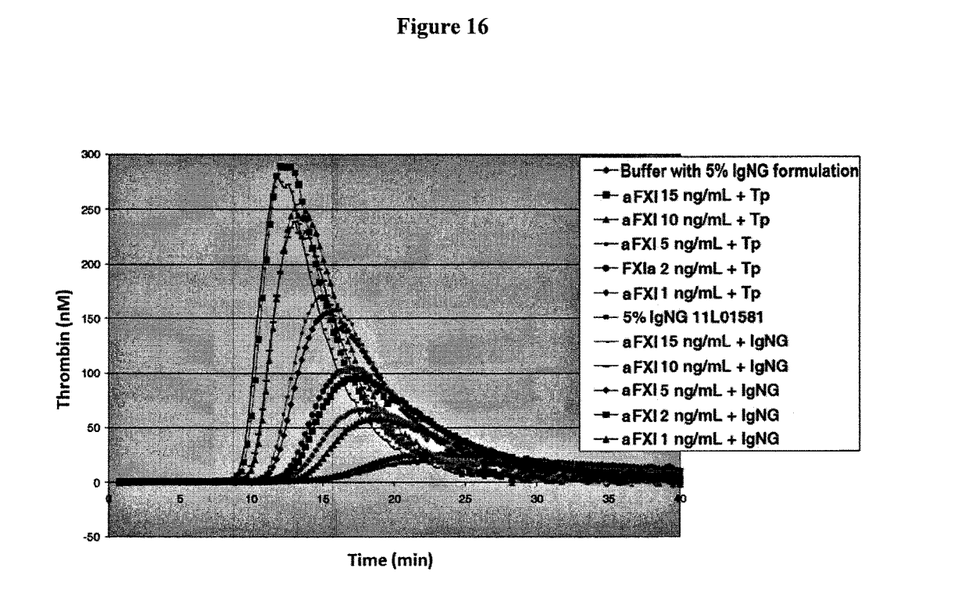
FIG. 16 represents the respective determination of the thrombogenic power of the samples containing respectively from 1 to 16 ng/ml of aFXI diluted in a batch of 5% IgNG or in the dilution buffer of said batch of 5% IgNG.

FIG. 16 shows that the thrombin generation profiles do not differ significantly in the presence or absence of immunoglobulin. The absence of inhibitory effect linked to the immunoglobulins is demonstrated, even for very low concentrations of aFXI, of the order of ng/ml.

Example 10: Determination of the Thrombogenic Power of Factor aVII

Figure 17A:
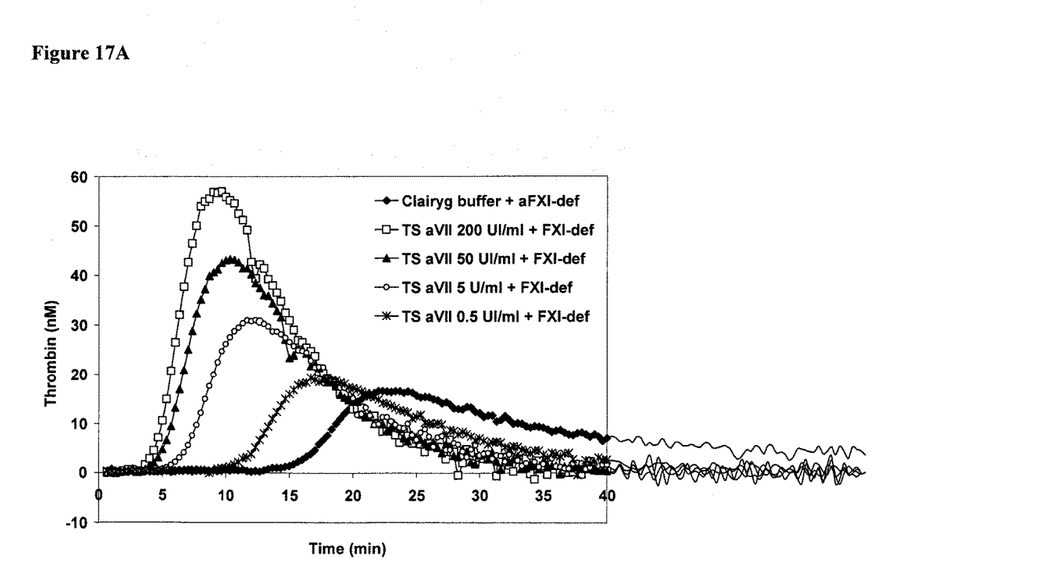
FIG. 17A represents the respective determination of the thrombogenic power of the samples containing respectively from 0.5 UI/ml to 200 UI/ml of aFVII in a plasma deficient in FXI or of Clairyg® buffer (buffer with the formulation of the Clairyg® product marketed by LFB BIOMEDICAMENTS) in a plasma deficient in FXI.
Figure 17B:
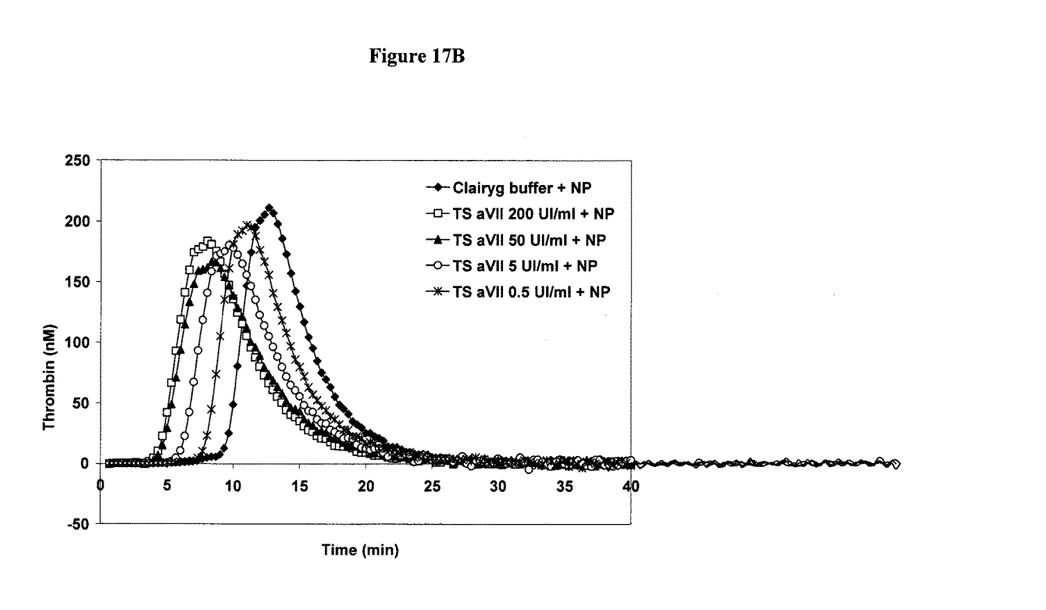
FIG. 17B represents the respective determination of the thrombogenic power of the samples containing respectively from 0.5 UI/ml to 200 UI/ml of aFVII in a normal plasma or of Clairyg® buffer in a normal plasma.

FIG. 17A and FIG. 17B show that the use of the kit of the present invention containing a human blood plasma deficient in aFXI makes it possible to give better sensitivity to the possible presence of Factor aVII in a sample to be tested relative to that obtained with a normal plasma.

Example 11: Determination of the Thrombogenic Power of Factor aIX

Figure 18A:
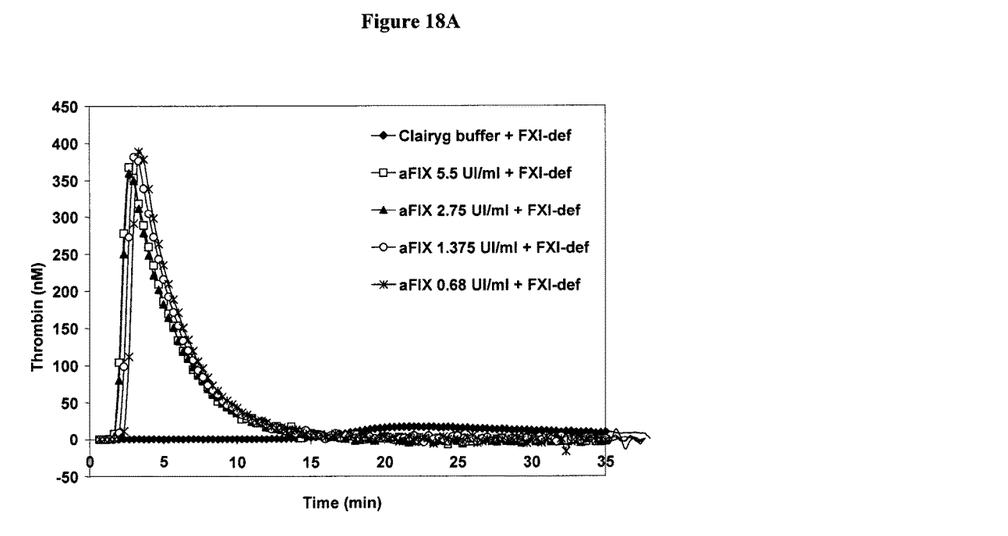
FIG. 18A represents the respective determination of the thrombogenic power of the samples containing respectively from 0.68 UI/ml to 5.5 UI/ml of aFIX in a plasma deficient in FXI or of Clairyg® buffer in a plasma deficient in FXI.
Figure 18B:
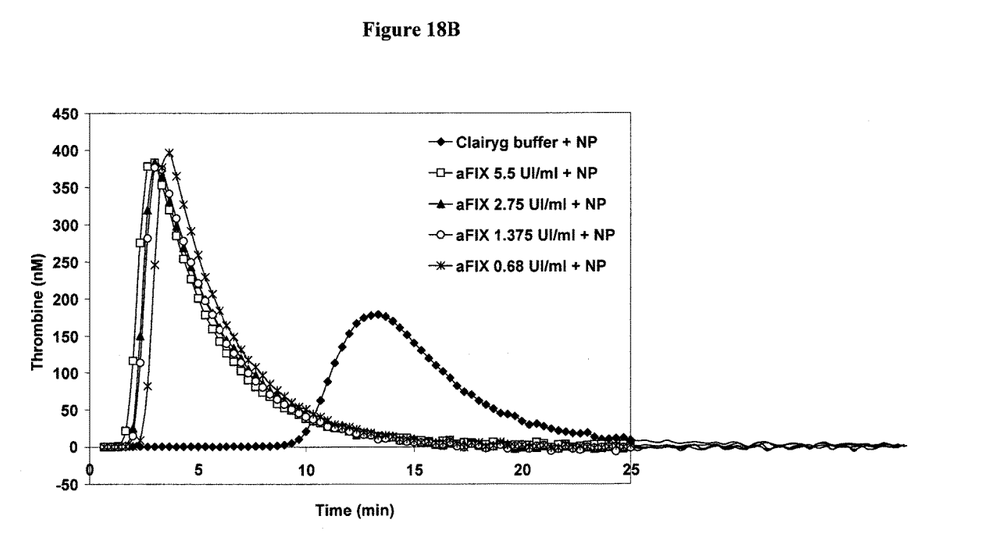
FIG. 18B represents the respective determination of the thrombogenic power of the samples containing respectively from 0.68 UI/ml to 5.5 UI/ml of aFIX in a normal plasma or of Clairyg® buffer in a normal plasma.

FIG. 18A and FIG. 18B show that the use of the kit of the present invention containing a human blood plasma deficient in FXI makes it possible to give better sensitivity to the possible presence of Factor aIX in a sample to be tested relative to that obtained with a normal plasma.

The invention claimed is:

1. A process for determining the thrombogenic power of human immunoglobulins for therapeutic use contained in a sample to be tested, with a kit comprising the following components:
a platelet-poor human blood plasma deficient in Factor XI (FXI),
phospholipids,
$CaCl_2$,
human tissue factor, and
a dilution buffer,
said process comprising the following stages:
mixing the components of the kit and the sample to be tested in order to form a reaction medium, wherein the final concentration of said human tissue factor in the reaction medium is 0.3 pM; and
obtaining a thrombinogram by carrying out a thrombin generation test on said reaction medium.

2. A process for determining the thrombogenic power of human immunoglobulins, linked to the presence of Factor VII, Factor XI, Factor IX, Factor X and/or of their activated forms in a sample to be tested, with a kit comprising the following components:
a platelet-poor human blood plasma deficient in Factor XI,
phospholipids,
$CaCl_2$,
human tissue factor, and
a dilution buffer,
said process comprising the following stages:
mixing the components of the kit and the sample to be tested in order to form a reaction medium, wherein the final concentration of said human tissue factor in the reaction medium is 0.3 pM; and
obtaining a thrombinogram by carrying out a thrombin generation test on said reaction medium.

3. The process according to claim 1, wherein the dilution buffer of said kit is identical to that of the sample to be tested.

4. The process according to claim 1, wherein said kit further comprises a fluorogenic substrate.

5. The process according to claim 1, wherein said kit comprises:
the platelet-poor human blood plasma deficient in FXI, the volume of which represents from 80% to 40% of the volume of the reaction medium,
human phospholipids, the final concentration of which in the reaction medium is from 1 µM to 10 µM,
the human tissue factor, the final concentration of which in the reaction medium is 0.3 pM, and
$CaCl_2$.

6. The process according to claim 1, wherein a ratio between the volume of the human blood plasma and that of the sample to be tested is from 8:1 to 2:1.

7. The process according to claim 1, wherein the human tissue factor of the kit is of plasma origin, of recombinant origin, or of transgenic origin.

8. The process according to claim 1, wherein the human blood plasma is a pool of fresh or frozen human blood plasmas or a calibrated commercial blood plasma.

9. A process for measuring the thrombogenic power of human immunoglobulins contained in a sample to be tested, comprising the following stages:
a) mixing a dilution buffer with a platelet-poor human blood plasma deficient in Factor XI (FXI) in order to form an intermediate negative control,
b) mixing a sample to be tested with the platelet-poor human blood plasma in order to form an intermediate reaction medium,
c) adding to the intermediate reaction medium obtained in stage b) and to the intermediate negative control obtained in stage a), a mixture comprising human phospholipids, $CaCl_2$, and 0.3 pM final concentration of human tissue factor, in order to form a reaction medium and a negative control;

d) obtaining a first thrombinogram by carrying out a thrombin generation test on the reaction medium obtained in stage c) and a second thrombinogram by carrying out a thrombin generation test on the negative control obtained in stage c);

e) comparing at least one of the parameters of each of the thrombinograms obtained in stage d) with a homologous parameter obtained from standard thrombinograms established on the basis of a series of calibrators the thrombogenic power of which linked to the presence of activated Factor VII, and/or activated Factor XI, and/or activated Factor IX, and/or activated Factor XII, and/or activated Factor X is known and varies between each calibrator; and f) determining from stage e), the thrombogenic power of human immunoglobulins contained in the sample to be tested.

10. The process according to claim 9, wherein the standard thrombinogram is obtained by carrying out a thrombin generation test on a reaction medium comprising: i) a calibrator, the thrombogenic power of which linked to the presence of activated Factor VII, and/or activated Factor XI, and/or activated Factor IX, and/or activated Factor XII, and/or activated Factor X is known, ii) a human blood plasma, iii) a reaction mixture comprising human phospholipids and human tissue factor.

11. The process according to claim 9, wherein the final concentration of the human phospholipids in the reaction medium is from 1 µM to 10 µM.

12. The process according to claim 9, wherein the volume of the human blood plasma represents from 80% to 40%, of the volume of the reaction medium.

13. The process according to claim 9, wherein a ratio between the volume of the human blood plasma and that of the sample to be tested is from 8:1 to 2:1.

14. Process according to claim 9, wherein the thrombinogram is obtained by the thromboelastography method or the thrombinography method.

15. A process for measuring the thrombogenic power of human immunoglobulins contained in a sample to be tested, comprising the following stages:

a) mixing a dilution buffer of a sample to be tested with a platelet-poor human blood plasma deficient in Factor XI in order to form an intermediate negative control;

b) mixing the sample to be tested with the platelet-poor human blood plasma deficient in Factor XI representing 53% of the volume of the reaction medium, in which the ratio between the volume of the blood plasma and that of the sample is from 8:1 to 2:1, in order to form an intermediate reaction medium;

c) adding to the intermediate reaction medium obtained in stage b) and to the intermediate negative control obtained in stage a), a mixture comprising 4 µM of phospholipids, and 0.3 pM of human tissue factor and $CaCl_2$, in order to form a reaction medium and a negative control;

d) obtaining two thrombinograms by the implementation of thrombinography, by carrying out a thrombin generation test on the reaction medium and on the negative control obtained in stage c);

e) comparing at least one of the parameters of each of the thrombinograms obtained in stage d) with a homologous parameter obtained from standard thrombinograms established on the basis of a series of calibrators the thrombogenic power of which linked to the presence of activated Factor VII, and/or activated Factor XI, and/or activated Factor IX, and/or activated Factor X is known and varies between each calibrator; and f) determining from stage e), the thrombogenic power linked to the presence of Factor VII, Factor XI, Factor IX, Factor X and/or of their activated form in the sample.

16. The process according to claim 1, wherein the sample to be tested is a biologically acceptable product.

17. The process according to claim 1, wherein said dilution buffer is a Tris NaCl buffer.

18. The process according to claim 5, wherein said kit comprises:

the platelet-poor human blood plasma deficient in FXI, the volume of which represents from 75% to 50% of the volume of the reaction medium, the human phospholipids, the final concentration of which in the reaction medium is from 1 µM to 10 µM, the human tissue factor, the final concentration of which in the reaction medium is 0.3 pM, and $CaCl_2$.

19. The process according to claim 5, wherein said kit comprises:

the platelet-poor human blood plasma deficient in FXI, the volume of which represents 53% of the volume of the reaction medium, the human phospholipids, the final concentration of which in the reaction medium is from 1 µM to 10 µM, the human tissue factor, the final concentration of which in the reaction medium is 0.3 pM, and $CaCl_2$.

20. The process according to claim 5, wherein said kit comprises:

the platelet-poor human blood plasma deficient in FXI, the volume of which represents from 80% to 40% of the volume of the reaction medium, the human phospholipids, the final concentration of which in the reaction medium is 4 µM, the human tissue factor, the final concentration of which in the reaction medium is 0.3 pM, and $CaCl_2$.

21. The process according to claim 6, wherein the ratio between the volume of the human blood plasma and that of the sample to be tested is 4:1.

* * * * *